(12) United States Patent
Taylor et al.

(10) Patent No.: US 11,311,413 B2
(45) Date of Patent: Apr. 26, 2022

(54) THERMAL SYSTEM WITH MEDICATION INTERACTION

(71) Applicant: Stryker Corporation, Kalamazoo, MI (US)

(72) Inventors: Gregory S. Taylor, Kalamazoo, MI (US); Robert Christopher Rusin, Richland, MI (US)

(73) Assignee: Stryker Corporation, Kalamazoo, MI (US)

( * ) Notice: Subject to any disclaimer, the term of this patent is extended or adjusted under 35 U.S.C. 154(b) by 855 days.

(21) Appl. No.: 16/169,271

(22) Filed: Oct. 24, 2018

(65) Prior Publication Data

US 2019/0125580 A1    May 2, 2019

Related U.S. Application Data

(60) Provisional application No. 62/577,772, filed on Oct. 27, 2017.

(51) Int. Cl.
*A61F 7/02* (2006.01)
*A61F 7/00* (2006.01)
(Continued)

(52) U.S. Cl.
CPC .............. *A61F 7/02* (2013.01); *A61F 7/0085* (2013.01); *A61M 5/44* (2013.01);
(Continued)

(58) Field of Classification Search
CPC ...... A61F 2007/0054; A61F 2007/0086; A61F 2007/0093; A61F 2007/0095;
(Continued)

(56) References Cited

U.S. PATENT DOCUMENTS 4,884,072 A   7/1989 French et al.
6,245,347 B1  6/2001 Zhang et al.
(Continued)

OTHER PUBLICATIONS

Altrix Precision Temperature Management System Stryker Operations Manuel, Dec. 2016.
(Continued)

*Primary Examiner* — Tigist S Demie
(74) *Attorney, Agent, or Firm* — Warner Norcross + Judd LLP

(57) ABSTRACT

A thermal control unit supplies temperature controlled fluid to a patient to control the patient's temperature. The thermal control unit includes a fluid outlet, fluid inlet, heat exchanger, pump, patient temperature probe port, user interface, and controller. The controller receives patient temperature readings from the patient temperature probe port and controls a temperature of the circulating fluid in a first manner when no event data is received regarding treatment of the patient. The controller controls a temperature of the circulating fluid in a second and different manner when event data is received. The event data may relate to medication and/or fluid administered to the patient. The different manners include determining a target fluid temperature in using different inputs and/or alarming in different manners. In some cases, the controller pauses the use of the patient temperature readings while continuing to deliver temperature controlled fluid to the patient.

19 Claims, 7 Drawing Sheets

(51) Int. Cl.
  *A61M 5/44* (2006.01)
  *A61M 5/172* (2006.01)
  *A61M 5/142* (2006.01)

(52) U.S. Cl.
  CPC .......... *A61F 2007/0054* (2013.01); *A61F 2007/0086* (2013.01); *A61F 2007/0093* (2013.01); *A61F 2007/0095* (2013.01); *A61F 2007/0096* (2013.01); *A61F 2007/0261* (2013.01); *A61M 5/14248* (2013.01); *A61M 5/172* (2013.01); *A61M 2205/36* (2013.01)

(58) Field of Classification Search
  CPC ...... A61F 2007/0096; A61F 2007/0261; A61F 7/0085; A61F 7/02; A61M 2205/36; A61M 5/14248; A61M 5/172; A61M 5/44
  See application file for complete search history.

(56) References Cited

U.S. PATENT DOCUMENTS

| | | |
|---|---|---|
| 6,830,581 B2 | 12/2004 | Magers |
| 8,647,374 B2 | 2/2014 | Koewler |
| 9,474,847 B2 | 10/2016 | Bonutti et al. |
| 2005/0058976 A1 | 3/2005 | Vernon |
| 2006/0122673 A1* | 6/2006 | Callister ............ A61F 7/12 607/105 |
| 2006/0195168 A1 | 8/2006 | Dunbar et al. |
| 2008/0082150 A1* | 4/2008 | Schock ............ A61F 7/0053 607/96 |
| 2008/0255641 A1 | 10/2008 | Ellis |
| 2008/0281297 A1 | 11/2008 | Pesach et al. |
| 2009/0254159 A1 | 10/2009 | Stormby |
| 2014/0200487 A1 | 7/2014 | Ramdas et al. |
| 2014/0343639 A1 | 11/2014 | Hopper et al. |
| 2017/0266036 A1 | 9/2017 | Taylor |
| 2017/0348144 A1 | 12/2017 | Taylor et al. |
| 2018/0014967 A1 | 1/2018 | Taylor |
| 2018/0042762 A1 | 2/2018 | Galer |
| 2018/0042763 A1 | 2/2018 | Galer et al. |
| 2018/0098878 A1 | 4/2018 | Kostic et al. |
| 2018/0140459 A1 | 5/2018 | Taylor et al. |
| 2018/0214301 A1 | 8/2018 | Fojtik et al. |
| 2018/0280191 A1 | 10/2018 | Taylor et al. |
| 2018/0325725 A1* | 11/2018 | Dabrowiak ............ A61F 7/12 |

OTHER PUBLICATIONS

"DigniCap How it Works—The Intelligent Scalp Cooling System", Dignitana Inc., 2017.
Arctic Sun 5000 Service Manual by Medivance, Inc., 2010-2011.
Gaymar Medi-Therm III, Hyper/Hypothermia Machine Ref MTA7912 Service Manual, Nov. 2009.
Sorin Group, Heater-Cooling System 3T, Operating Instructions, 2015.

* cited by examiner

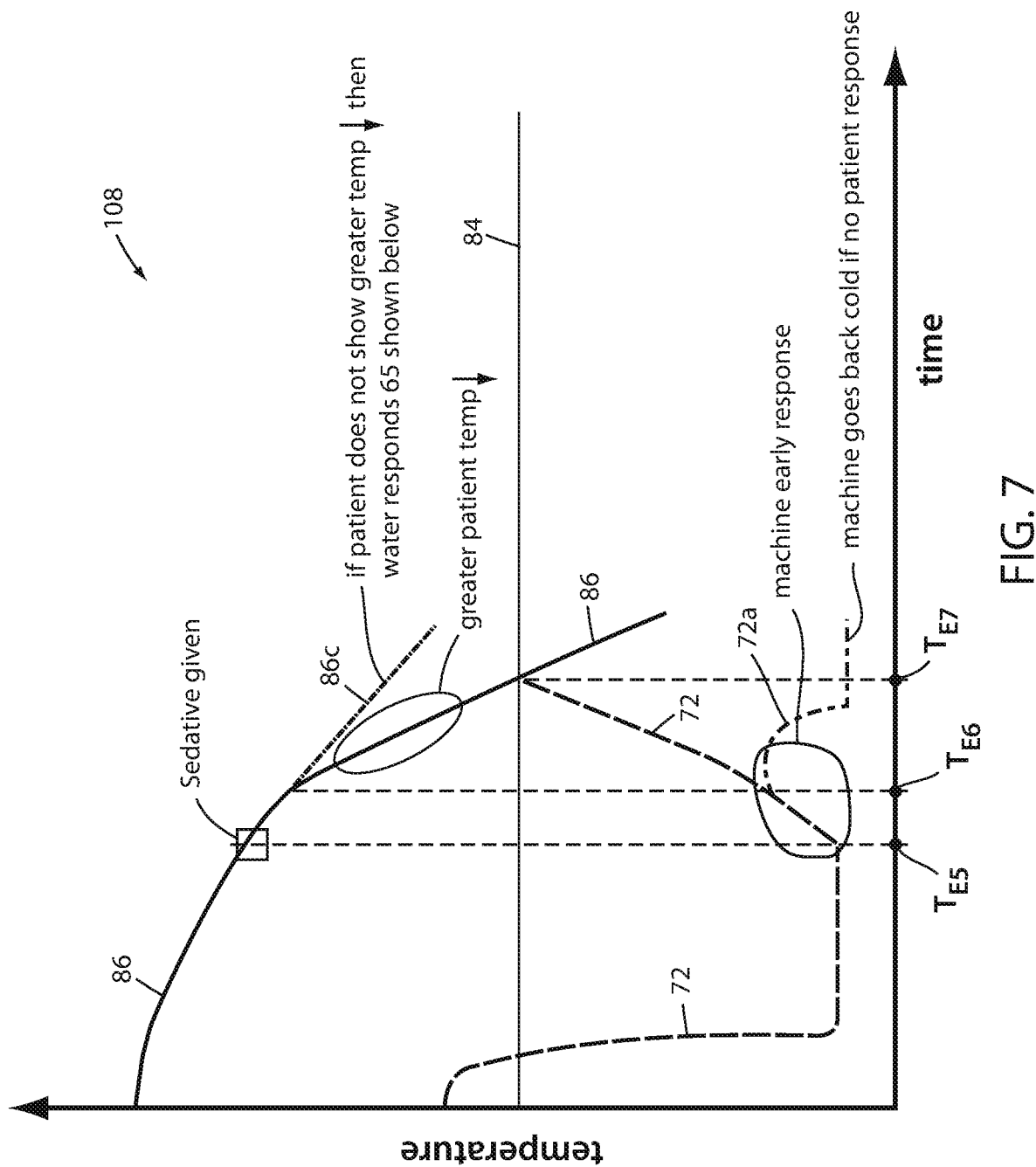

THERMAL SYSTEM WITH MEDICATION INTERACTION

CROSS-REFERENCE TO RELATED APPLICATIONS

This application claims priority to commonly assigned U.S. provisional patent application Ser. No. 62/577,772 filed Oct. 27, 2017, by inventors Gregory Taylor et al. and entitled THERMAL SYSTEM WITH MEDICATION INTERACTION, the complete disclosure of which is incorporated herein by reference.

BACKGROUND

The present invention relates to a thermal control system for controlling the temperature of circulating fluid that is delivered to one or more thermal pads positioned in contact with a patient.

Thermal control systems are known in the art for controlling the temperature of a patient by providing a thermal control unit that supplies temperature controlled fluid to one or more thermal pads positioned in contact with a patient and/or to one or more catheters positioned inside the patient. The thermal control unit includes one or more heat exchangers for controlling the temperature of the fluid and a pump that pumps the temperature controlled fluid to the pad(s) and/or catheter(s). After passing through the pad(s) or catheter(s), the fluid is returned to the thermal control unit where any necessary adjustments to the temperature of the returning fluid are made before being pumped back to the pad(s) and/or catheter(s).

In some instances, the temperature of the fluid is controlled to a static target temperature, while in other instances the temperature of the fluid is varied as necessary in order to automatically effectuate a target patient temperature. When the thermal control unit automatically controls the temperature of the circulating fluid in order to effectuate a desired patient temperature, the thermal control unit utilizes patient temperature measurements in a closed-loop feedback manner. The closed loop feedback gives the thermal control unit knowledge of the patient's temperature, which it uses to determine whether to heat or cool the circulating fluid, or to maintain the circulating fluid at its current temperature.

SUMMARY

In some instances, the temperature readings from one or more patient temperature probes provide patient temperature information that is not indicative of the action of the thermal control unit in controlling the patient's temperature. For example, in some instances, the patient undergoing thermal treatment is given one or more medications that are known to raise or lower the patient's temperature. In other instances, the patient is given a medication or fluid at a location adjacent to the patient temperature probe, and the temperature of the medication or fluid changes the temperature measured by the patient temperature probe. According to some embodiments, the present disclosure provides an improved thermal control unit that addresses these and other situations where the patient temperature readings are affected by one or more extraneous events. The present disclosure also provides an improved thermal control unit that allows automatic selecting of patient target temperatures in response to one or more extraneous events, such as, but not limited to, the administration of one or more medications to the patient.

According to one embodiment of the present disclosure, a thermal control unit for controlling the temperature of a patient is provided. The thermal control unit includes a fluid outlet, fluid inlet, heat exchanger, pump, user interface, and controller. The fluid outlet is adapted to fluidly couple to a fluid supply line and the fluid inlet is adapted to fluidly couple to a fluid return line. The pump circulates fluid from the fluid inlet through the heat exchanger and to the fluid outlet. The user interface receives event data regarding a patient treatment event. The controller controls a temperature of the circulating fluid in a first manner if event data is not received and controls a temperature of the circulating fluid in a second manner if event data is received, wherein the first manner is different from the second manner.

According to another aspect of the present disclosure, the event data indicates administration of a medication to the patient. The second manner may include supplying warmer circulating fluid to the patient than the first manner if the medication is one of a paralytic and a sedative.

In some embodiments, the first manner includes controlling the temperature of the circulating fluid using actual patient temperature readings and the second manner includes controlling the temperature of the circulating fluid using assumed patient temperature readings.

The controller may operate in the second manner for a predefined amount of time and thereafter automatically switch back to operating in the first manner.

According to some embodiments, the thermal control unit further comprises a patient temperature probe port adapted to receive patient temperature readings from a patient temperature probe. In such embodiments, the first manner includes using the patient temperature readings to control the temperature of the circulating fluid, and the second manner includes not using the patient temperature readings to control the temperature of the circulating fluid.

According to another aspect of the present disclosure, a thermal control unit is provided for controlling a temperature of a patient. The thermal control unit includes a fluid outlet, fluid inlet, circulation channel, pump, heat exchanger, fluid temperature sensor, patient temperature probe port, user interface, and controller. The fluid outlet is adapted to fluidly couple to a fluid supply line and the fluid inlet is adapted to fluidly couple to a fluid return line. The circulation channel is fluidly coupled to the fluid outlet and the fluid inlet. The pump circulates fluid through the circulation channel from the fluid inlet to the fluid outlet. The heat exchanger controls a temperature of the fluid circulating in the circulation channel. The fluid temperature sensor senses a temperature of the circulating fluid. The patient temperature probe port is adapted to receive patient temperature readings from a patient temperature probe. The user interface includes a pause control and an input for receiving a patient target temperature. The controller uses the patient temperature readings to control a temperature of the circulating fluid when the pause control is not activated and pauses using the patient temperature readings to control the temperature of the circulating fluid when the pause control is activated.

According to other aspects of the present disclosure, the controller pauses for a predefined amount of time, and thereafter resumes utilizing the patient temperature readings to control the temperature of the circulating fluid.

The controller continues to pump the circulating fluid out of the fluid outlet to the patient while the controller pauses its use of the patient temperature readings to control the temperature of the circulating fluid.

In some embodiments, the controller sets a target temperature of the circulating fluid to a value that is based on a current patient temperature reading when the pause control is not activated. When the pause control is activated, the controller sets a target temperature of the circulating fluid to a value that is based on a previous patient temperature reading.

In some embodiments, the controller uses actual patient temperature readings to control a temperature of the circulating fluid when the pause control is not activated and uses assumed patient temperature readings when the pause control is activated. The assumed patient temperature readings may be predicted from past temperature readings, may be inferred from other readings (e.g. an amount of heat transferred to/from the patient), and/or may be generated from a combination of predictions and inferences.

The controller may record a patient temperature reading when pausing the use of patient temperature readings to control the temperature of the circulating fluid. When so recorded, the controller continues to pause until a current patient temperature reading returns to within a threshold of the recorded patient temperature reading.

The user interface, in some embodiments, is adapted to allow a user to indicate a type of event regarding patient treatment. The type of event includes at least one of the following: a particular medication administered to the patient and fluid administered to the patient at a location adjacent to the patient temperature probe (such as fluid used to clean or flush a patient temperature probe, or fluid used for other purposes).

The controller may pause using the patient temperature readings for varying amounts of time based on at least one of the following: the particular medication, the amount of the particular medication, and/or the amount of fluid applied to the patient at the situs of the patient temperature probe.

According to another embodiment of the present disclosure, a thermal control unit for controlling a temperature of a patient is provided. The thermal control unit includes a fluid outlet, fluid inlet, circulation channel, pump, heat exchanger, fluid temperature sensor, patient temperature probe port, user interface, and controller. The fluid outlet is adapted to fluidly couple to a fluid supply line and the fluid inlet is adapted to fluidly couple to a fluid return line. The circulation channel fluidly couples the fluid outlet and the fluid inlet. The pump circulates fluid through the circulation channel from the fluid inlet to the fluid outlet. The heat exchanger controls a temperature of the fluid circulating in the circulation channel. The fluid temperature sensor senses a temperature of the circulating fluid and the patient temperature probe port is adapted to receive patient temperature readings from a patient temperature probe. The user interface is adapted to receive a patient target temperature and event data regarding a patient treatment event. The controller issues an alarm if the patient temperature readings deviate from a predefined criterion when no event data is entered via the user interface. The controller also is adapted to not issue the alarm if the patient temperature readings deviate from the predefined criterion when event data is entered via the user interface.

According to other aspects, when event data is entered via the user interface, the controller does not issue the alarm for a predefined time period, which may be a fixed amount of time or it may be a variable amount of time that lasts until a current patient temperature reading returns to within a threshold of a previous patient temperature reading recorded prior to the event data being entered. However measured, after expiration of the predefined time period, the controller issues the alarm if the patient temperature readings deviate from the predefined criterion.

In some embodiments, the predefined criterion is a maximum rate of change of the patient temperature readings coming from the patient temperature probe.

In some embodiments, the controller uses the patient temperature readings to control a temperature of the circulating fluid when no event data is received, and pauses using the patient temperature readings to control the temperature of the circulating fluid when event data is received. When pausing the use of patient temperature readings to control the temperature of the circulating fluid, the controller continues to pump the circulating fluid out of the fluid outlet to the patient.

Also or additionally, the controller may be configured to set a target temperature of the circulating fluid to a value that is based on a current patient temperature reading when no event data is received, and set a target temperature of the circulating fluid to a value that is based on a previous patient temperature reading when event data is received. The previous patient temperature reading may be used to predict a current patient temperature reading.

According to another embodiment of the present disclosure, a thermal control unit for controlling a temperature of a patient is provided. The thermal control unit includes a fluid outlet, fluid inlet, circulation channel, pump, heat exchanger, fluid temperature sensor, patient temperature probe port, user interface, and controller. The fluid outlet is adapted to fluidly couple to a fluid supply line and the fluid inlet is adapted to fluidly couple to a fluid return line. The circulation channel is coupled to the fluid outlet and the fluid inlet and the pump circulates fluid through the circulation channel from the fluid inlet to the fluid outlet. The heat exchanger controls a temperature of the fluid circulating in the circulation channel. The fluid temperature sensor senses a temperature of the circulating fluid and the patient temperature probe port receives patient temperature readings from a patient temperature probe. The user interface receives a patient target temperature and event data regarding a patient treatment event. The controller uses the patient temperature readings to control a temperature of the circulating fluid when no event data is received, and uses assumed patient temperature readings when event data is received.

According to other aspects, the assumed patient temperature readings are generated by the controller based upon a trend in the patient's temperature readings prior to the event data being received.

The controller, in some embodiments, uses the assumed patient temperature readings to determine a target temperature for the circulating fluid.

In some embodiments, the controller uses assumed patient temperature readings for a predefined time period.

The controller may also or alternatively predict an expected patient temperature reading at an expiration of the predefined time period. The predefined time period is one of a fixed amount of time and a variable amount of time that lasts until a current patient temperature reading falls within a predefined range of the expected patient temperature.

Before the various embodiments disclosed herein are explained in detail, it is to be understood that the claims are not to be limited to the details of operation or to the details of construction, nor to the arrangement of the components set forth in the following description or illustrated in the drawings. The embodiments described herein are capable of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the claims to any specific order or number of components. Nor should the use of enumeration be construed as excluding from the scope of the claims any additional steps or components that might be combined with or into the enumerated steps or components.

BRIEF DESCRIPTION OF THE DRAWINGS

FIG. 7 is a graph of a patient target temperature, patient measured temperature, and fluid temperature illustrating a second manner of response of the thermal control unit to the administration of a sedative to the patient.

DETAILED DESCRIPTION OF THE EMBODIMENTS

Figure 1:
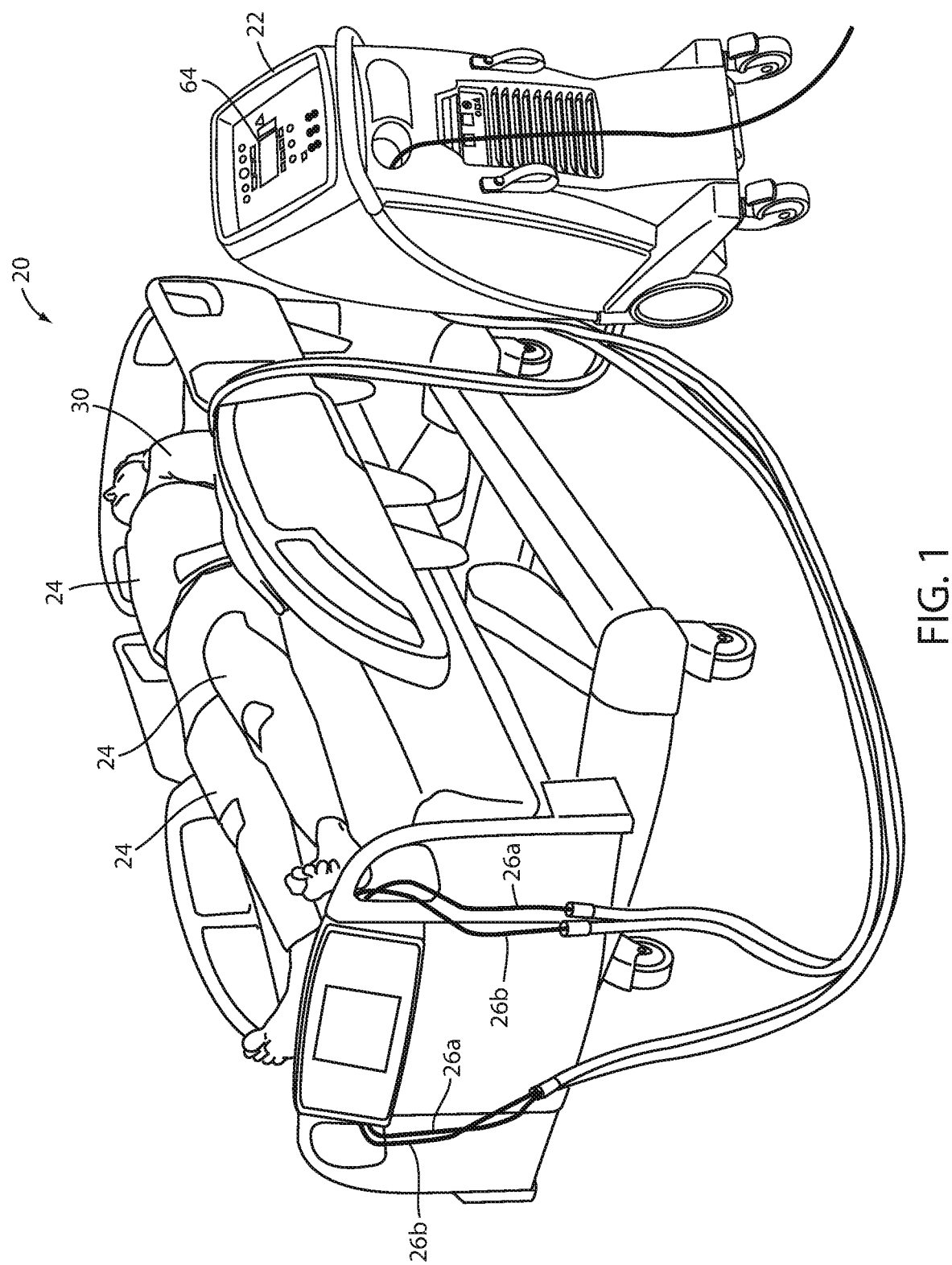
FIG. 1 is a perspective view of a thermal control system according to one aspect of the present disclosure shown applied to a patient on a patient support apparatus.

A thermal control system 20 according to one embodiment of the present disclosure is shown in FIG. 1. Thermal control system 20 is adapted to control the temperature of a patient 30, which may involve raising, lowering, or maintaining the patient's temperature, or combinations thereof. Thermal control system 20 includes a thermal control unit 22 coupled to one or more thermal therapy devices 24. The thermal therapy devices 24 are illustrated in FIG. 1 to be thermal pads, but it will be understood that thermal therapy devices 24 may take on other forms, such as, but not limited to, blankets, vests, patches, caps, catheters, or other structures that receive temperature controlled fluid. For purposes of the following written description, thermal therapy devices 24 will be referred to as thermal pads 24, but it will be understood by those skilled in the art that this terminology is used merely for convenience and that the phrase "thermal pad" is intended to cover all of the different variations of thermal therapy devices 24 mentioned above (e.g. blankets, vests, patches, caps, catheters, etc.).

Thermal control unit 22 is coupled to thermal pads 24 via a plurality of hoses 26. Thermal control unit 22 delivers temperature controlled fluid (such as, but not limited to, water or a water mixture) to the thermal pads 24 via the fluid supply hoses 26a. After the temperature controlled fluid has passed through thermal pads 24, thermal control unit 22 receives the temperature controlled fluid back from thermal pads 24 via the return hoses 26b.

In the embodiment of thermal control system 20 shown in FIG. 1, three thermal pads 24 are used in the treatment of patient 30. A first thermal pad 24 is wrapped around a patient's torso, while second and third thermal pads 24 are wrapped, respectively, around the patient's right and left legs. Other configurations can be used and different numbers of thermal pads 24 may be used with thermal control unit 22, depending upon the number of inlet and outlet ports that are included with thermal control unit 22. By controlling the temperature of the fluid delivered to thermal pads 24 via supply hoses 26a, the temperature of the patient 30 can be controlled via the close contact of the pads 24 with the patient 30 and the resultant heat transfer therebetween.

Figure 3:
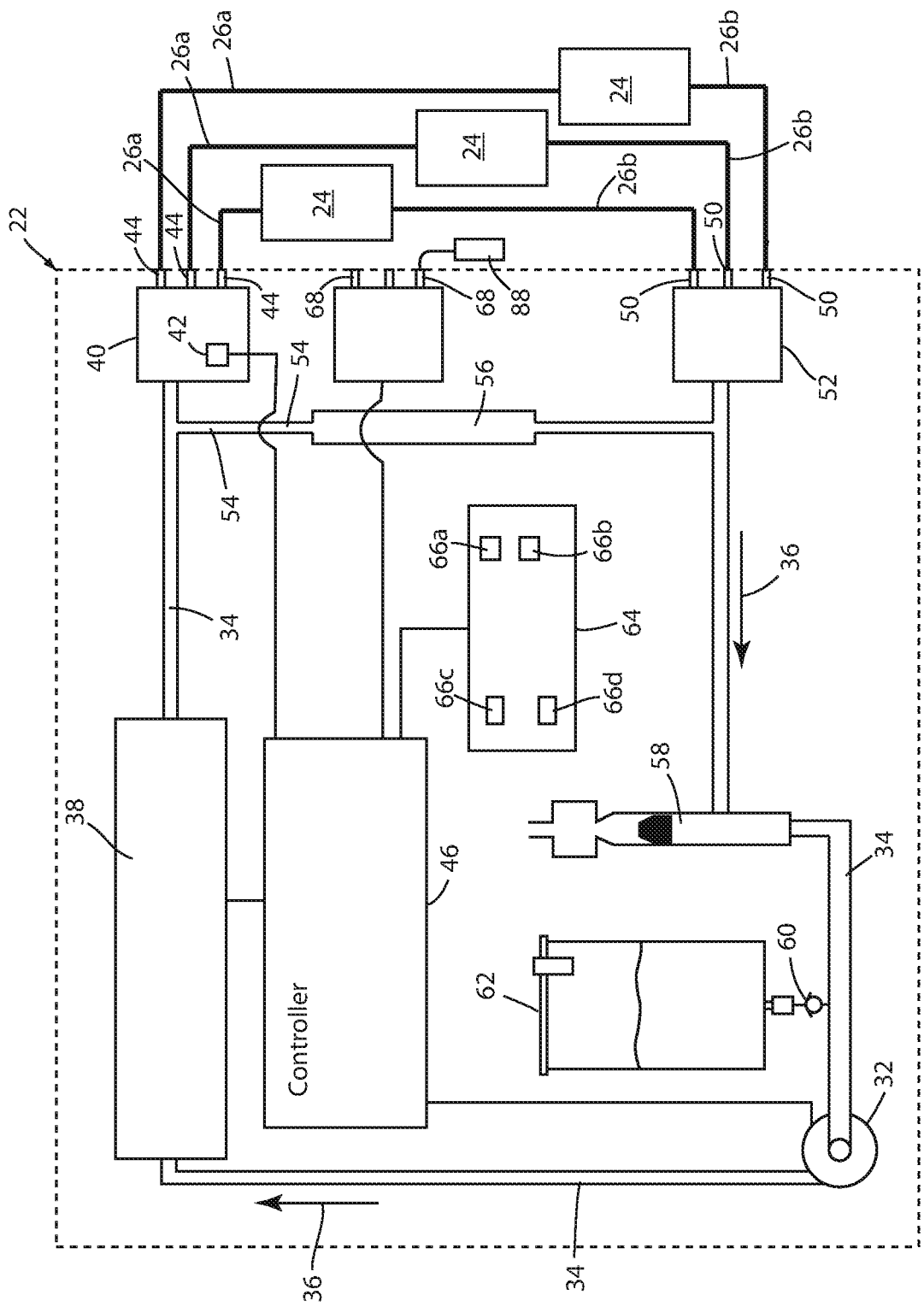
FIG. 3 is a block diagram of a control system for the thermal control unit of FIGS. 1 & 2.

Thermal control unit 22 is adapted to raise or lower the temperature of the fluid supplied to thermal pads 24. As shown in FIG. 3, thermal control unit 22 includes a pump 32 for circulating fluid through a circulation channel 34. Pump 32, when activated, circulates the fluid through circulation channel 34 in the direction of arrows 36 (clockwise in FIG. 3). Starting at pump 32 the circulating fluid first passes through a heat exchanger 38 where it is delivered to an outlet manifold 40 having an outlet temperature sensor 42 and a plurality of outlet ports 44. Temperature sensor 42 is adapted to detect a temperature of the fluid inside of outlet manifold 40 and report it to a controller 46.

Outlet ports 44 are coupled to supply hoses 26a. Supply hoses 26a are coupled, in turn, to thermal pads 24 and deliver temperature controlled fluid to the thermal pads 24. The temperature controlled fluid, after passing through the thermal pads, is returned to thermal control unit 22 via return hoses 26b. Return hoses 26b couple to a plurality of inlet ports 50. Inlet ports 50 are fluidly coupled to an inlet manifold 52 inside of thermal control unit 22.

Control unit 22 also includes a bypass line 54 fluidly coupled to outlet manifold 40 and inlet manifold 52 (FIG. 3). Bypass line 54 allows fluid to circulate through circulation channel 34 even in the absence of any thermal pads 24 or hoses 26a being coupled to any of outlet ports 44. In the illustrated embodiment, bypass line 54 includes an optional filter 56 that is adapted to filter the circulating fluid. If included, filter 56 may be a particle filter adapted to filter out particles within the circulating fluid that exceed a size threshold, or filter 56 may be a biological filter adapted to purify or sanitize the circulating fluid, or it may be a combination of both. In some embodiments, filter 56 is constructed and/or positioned within thermal control unit 22 in any of the manners disclosed in commonly assigned U.S. patent application Ser. No. 62/404,676 filed Oct. 11, 2016, by inventors Marko Kostic et al. and entitled THERMAL CONTROL SYSTEM, the complete disclosure of which is incorporated herein by reference.

Figure 2:
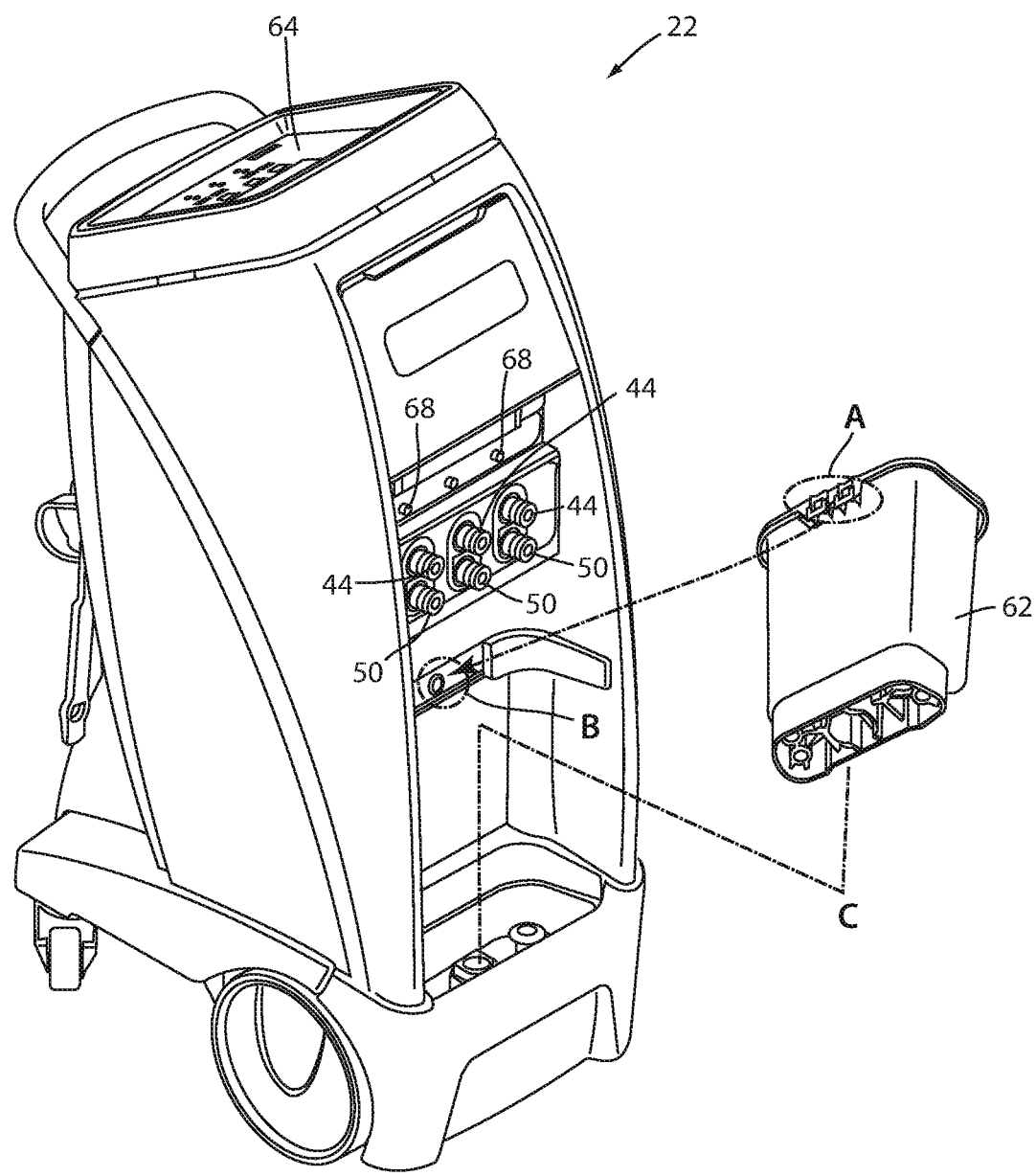
FIG. 2 is a perspective view of the thermal control unit of the thermal control system of FIG. 1.

The incoming fluid flowing into inlet manifold 52 from inlet ports 50 and bypass line 54 travels back toward the pump 32 into an air separator 58. Air separator 58 includes any structure in which the flow of fluid slows down sufficiently to allow air bubbles contained within the circulating fluid to float upwardly and escape to the ambient surrounding. In some embodiments, air separator 58 is constructed in accordance with any of the configurations disclosed in commonly assigned U.S. patent application Ser. No. 62/361,124 filed Jul. 12, 2016, by inventor Gregory S. Taylor and entitled THERMAL CONTROL SYSTEM, the complete disclosure of which is hereby incorporated herein by reference. After passing through air separator 58, the circulating fluid flows past a valve 60 positioned beneath a fluid reservoir 62. Fluid reservoir 62 supplies fluid to thermal control unit 22 and circulation channel 34 via valve 60, which may be a conventional check valve, or other type of valve, that automatically opens when reservoir 62 is coupled to thermal control unit 22 and that automatically closes when reservoir 62 is decoupled from thermal control unit 22 (see FIG. 2). After passing by valve 60, the circulating fluid travels to pump 32 and the circuit is repeated.

Controller 46 of thermal control unit 22 is contained within a main body of thermal control unit 22 and is in electrical communication with pump 32, heat exchanger 38, outlet temperature sensor 42, and a user interface 64. Controller 46 includes any and all electrical circuitry and components necessary to carry out the functions and algorithms described herein, as would be known to one of ordinary skill in the art. Generally speaking, controller 46 may include one or more microcontrollers, microprocessors, and/or other programmable electronics that are programmed to carry out the functions described herein. It will be understood that controller 46 may also include other electronic components that are programmed to carry out the functions described herein, or that support the microcontrollers, microprocessors, and/or other electronics. The other electronic components include, but are not limited to, one or more field programmable gate arrays, systems on a chip, volatile or nonvolatile memory, discrete circuitry, integrated circuits, application specific integrated circuits (ASICs) and/or other hardware, software, or firmware, as would be known to one of ordinary skill in the art. Such components can be physically configured in any suitable manner, such as by mounting them to one or more circuit boards, or arranging them in other manners, whether combined into a single unit or distributed across multiple units. Such components may be physically distributed in different positions in thermal control unit 22, or they may reside in a common location within thermal control unit 22. When physically distributed, the components may communicate using any suitable serial or parallel communication protocol, such as, but not limited to, CAN, LIN, Firewire, I-squared-C, RS-232, RS-465, universal serial bus (USB), etc.

User interface 64, which may be implemented as a control panel or in other manners, allows a user to operate thermal control unit 22. User interface 64 communicates with controller 46 and includes controls enabling a user to turn control unit 22 on and off, one or more controls enabling the user to select a target temperature for the fluid delivered to thermal pads 24, at least one control 66a allowing a user to set a target patient temperature, a pause/event control 66b, a medication control 66c, an automatic temperature adjustment control 66d, and/or other controls. Pause/event control 66b allows a user to pause the use of patient temperature readings from a patient temperature probe 88 (FIG. 3) during thermal treatment of the patient, as will be explained in greater detail below. In some embodiments, pause/event control 66b may be separated into multiple controls: one for carrying out a pause and another for inputting event data. In still other embodiments, the functions associated with pause/event control 66b may be accessed and/or controlled in other manners, such as through the use of one or more switches, buttons, dials, and/or the like. Medication control 66c and temperature adjustment control 66d are explained in greater detail below and, in some embodiments, may be combined with pause/event control 66b and/or each other. In some embodiments, user interface 64 may be located and/or duplicated at an off-board location, such as on a smart phone, a portable computer, a dedicated remote control for thermal control unit 22, and/or on other devices and/or at other locations.

In some embodiments, user interface 64 also allows a user to select from different modes for controlling the patient's temperature. These include, but are not limited to, a manual mode and an automatic mode, both of which may be used for cooling and heating the patient. In the manual mode, a user selects a target temperature for the fluid that circulates within thermal control unit 22 and that is delivered to thermal pads 24. Control unit 22 then makes adjustments to heat exchanger 38 in order to ensure that the temperature of the fluid exiting supply hoses 26a is at the user-selected temperature.

Another one of the modes is an automatic mode. When the user selects the automatic mode, the user selects a target patient temperature, rather than a target fluid temperature. After selecting the target patient temperature, controller 46 makes automatic adjustments to the temperature of the fluid in order to bring the patient's temperature to the desired patient target temperature. In this mode, the temperature of the circulating fluid may vary as necessary in order to bring about the target patient temperature.

In order to carry out the automatic mode, thermal control unit 22 includes one or more patient temperature probe ports 68 (FIGS. 2 & 3) that are adapted to receive one or more conventional patient temperature probes 88. The patient temperature probes may be any suitable patient temperature probe that is able to sense the temperature of the patient at the location of the probe. In one embodiment, the patient temperature probes are conventional Y.S.I. 400 probes marketed by YSI Incorporated of Yellow Springs, Ohio, or probes that are YSI 400 compliant. In other embodiments, different types of probes may be used with thermal control unit 22. Regardless of the specific type of patient temperature probe used in system 20, each temperature probe is connected to a patient temperature probe port 68 positioned on control unit 22. Patient temperature probe ports 68 are in electrical communication with controller 46 and provide current temperature readings of the patient's temperature.

Figure 4:
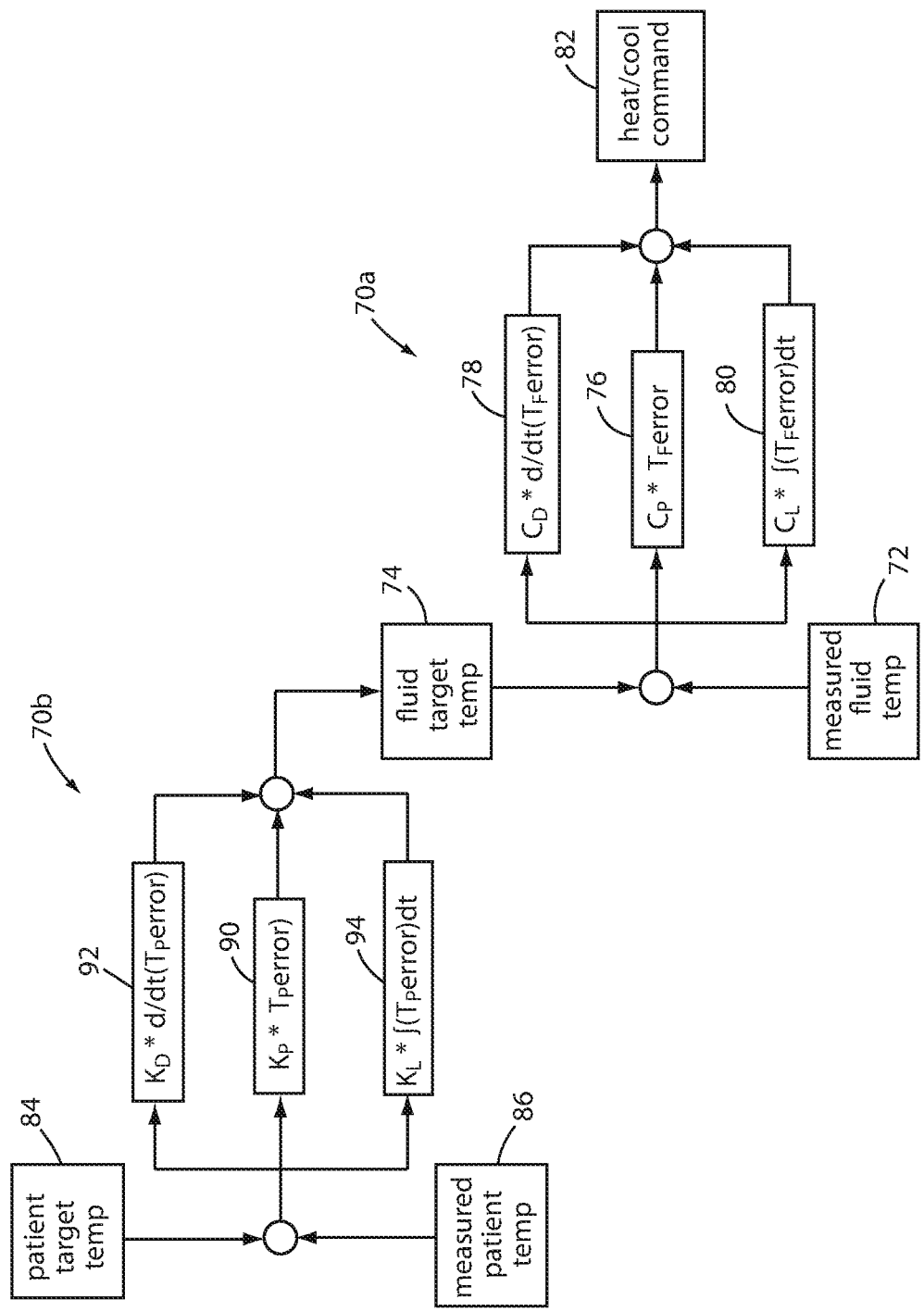
FIG. 4 is an illustrative control loop diagram followed in at least one embodiment of the thermal control unit of FIGS. 1 & 2.

FIG. 4 illustrates a pair of feedback loops 70a and 70b that are used in at least one embodiment of thermal control unit 22. Feedback loop 70a is used by controller 46 when thermal control unit 22 is operating in the manual mode and feedback loops 70a and 70b are both used by controller 46 when thermal control unit 22 is operating in the automatic mode. Feedback loop 70a uses a measured fluid temperature 72 and a fluid target temperature 74 as inputs. Measured fluid temperature 72 comes from outlet temperature sensor 42. Fluid target temperature 74, when thermal control unit 22 is operating in the manual mode, comes from a user inputting a desired fluid temperature. When thermal control unit 22 is operating in the automatic mode, fluid target temperature 74 comes from the output of control loop 70b, as discussed more below.

Control loop 70a determines the difference between the fluid target temperature 74 and the measured fluid temperature 72 ($T_f$error) and uses the resulting error value as an input into a conventional Proportional, Integral, Derivative (PID) control loop. That is, controller 46 multiplies the fluid temperature error by a proportional constant ($C_P$) at step 76, determines the derivative of the fluid temperature error over time and multiplies it by a constant ($C_D$), and determines the integral of the fluid temperature error over time and multiplies it by a constant ($C_I$) at step 80. The results of steps 76, 78, and 80 are summed together and converted to a heating/cooling command at step 82. The heating/cooling command is fed to heat exchanger 38 and tells heat exchanger 38 whether to heat and/or cool the circulating fluid and how much heating/cooling power to use.

Control loop 70b which, as noted, is used during the automatic mode, determines the difference between a patient target temperature 84 and a measured patient temperature 86. Patient target temperature 84 is input by a user of thermal control unit 22 using control 66a of user interface 64. Measured patient temperature 86 comes from a patient temperature probe 88 coupled to one of patient temperature probe ports 68. Controller 46 determines the difference between the patient target temperature 84 and the measured patient temperature 86 ($T_p$error) and uses the resulting patient temperature error value as an input into a conventional PID control loop. As part of the PID loop, controller 46 multiples the patient temperature error by a proportional constant ($K_P$) at step 90, multiplies a derivative of the patient temperature error over time by a derivative constant ($K_D$) at step 92, and multiplies an integral of the patient temperature error over time by an integral constant ($K_I$) at step 94. The results of steps 90, 92, and 94 are summed together and converted to a target fluid temperature value 74. The target fluid temperature value 74 is then fed to control loop 70a, which uses it to compute a fluid temperature error, as discussed above.

It will be understood by those skilled in the art that although FIG. 4 illustrates two PID control loops 70a and 70b, other types of control loops may be used. For example, loops 70a and/or 70b can be replaced by one or more PI loops, PD loops, and/or other types of control equations. Controller 46 implements loops 70a and/or 70b multiple times a second in at least one embodiment, although it will be understood that this rate may be varied widely. After controller 46 has output a heat/cool command at step 82 to heat exchanger 38, controller 46 takes another patient temperature reading 86 and/or another fluid temperature reading 72 and re-performs loops 70a and/or 70b. The specific loop(s) used, as noted previously, depends upon whether thermal control unit 22 is operating in the manual mode or automatic mode.

When thermal control unit 22 is operating in the automatic mode, controller 46 continuously implements control loops 70b and 70a. However, if a user activates pause/event control 66b, controller 46 carries out control loops 70b and 70a in a manner different than it does when pause/event control 66b is not activated. Specifically, when pause/event control 66b is not activated, control loop 70b is executed by controller 46 using measured patient temperatures 86 that come from patient temperature probe 88. However, when pause/event control 66b is activated, controller 46 modifies control loop 70b so that, instead of using measured patient temperature 86 that come from patient temperature probe 88, controller uses one or more assumed patient temperatures. The assumed patient temperatures are used by controller 46 in loop 70b in the same manner as the actual measured patient temperatures 86 are used in loop 70b. That is, controller 46 compares the patient target temperature to the assumed patient temperature and determines the difference, if any. This difference is then forwarded to the proportional, derivative, and integral channels of control loop 70a where it is processed in the manners described above with respect to steps 90, 92, and 94. After steps 90, 92, and 94, the outputs from these steps are summed together to determine a fluid target temperature, and the fluid target temperature is input into control loop 70a.

Controller 46 utilizes one or more assumed patient temperature readings after pause/event control 66b is activated because pause/event control 66b is intended to be activated when a patient is given medication, has fluid applied to the situs of patient temperature probe 88 for cleaning (or other) purposes, or experiences some other type of treatment that affects the temperature readings of patient temperature probe 88. For example, in many cases it is customary to use a patient temperature probe 88 that is positioned in a patient's esophagus. Medication, however, may also be delivered to a patient via his or her esophagus during thermal treatment of the patient, or the esophagus and/or the temperature probe 88 may be rinsed with fluid during thermal treatment of the patient. When such medication and/or other fluids are given to the patient, they are typically not at the same temperature of the patient. In some cases, they may be at room temperature, or they may be refrigerated, or in some cases heated.

As a result, when the fluid or medication is administered to the patient at a location adjacent to the patient temperature probe 88, the patient temperature probe begins reporting patient temperatures that are no longer an accurate reflection of the patient's actual temperature. This is because the administered fluid or medication comes into physical contact with the patient temperature probe 88 and the probe begins reporting temperatures of the fluid and/or medication, or temperatures that are a combination of the patient's temperature mixed with the fluid and/or medication's temperature. In the absence of the activation of pause/event control 66b, these inaccurate patient temperature readings cause controller 46 to change its thermal control of the fluid circulating in circulation channel 34. However, this change in thermal control is based on inaccurate temperature information and can interrupt and/or delay the thermal treatment of the patient.

Figure 5:
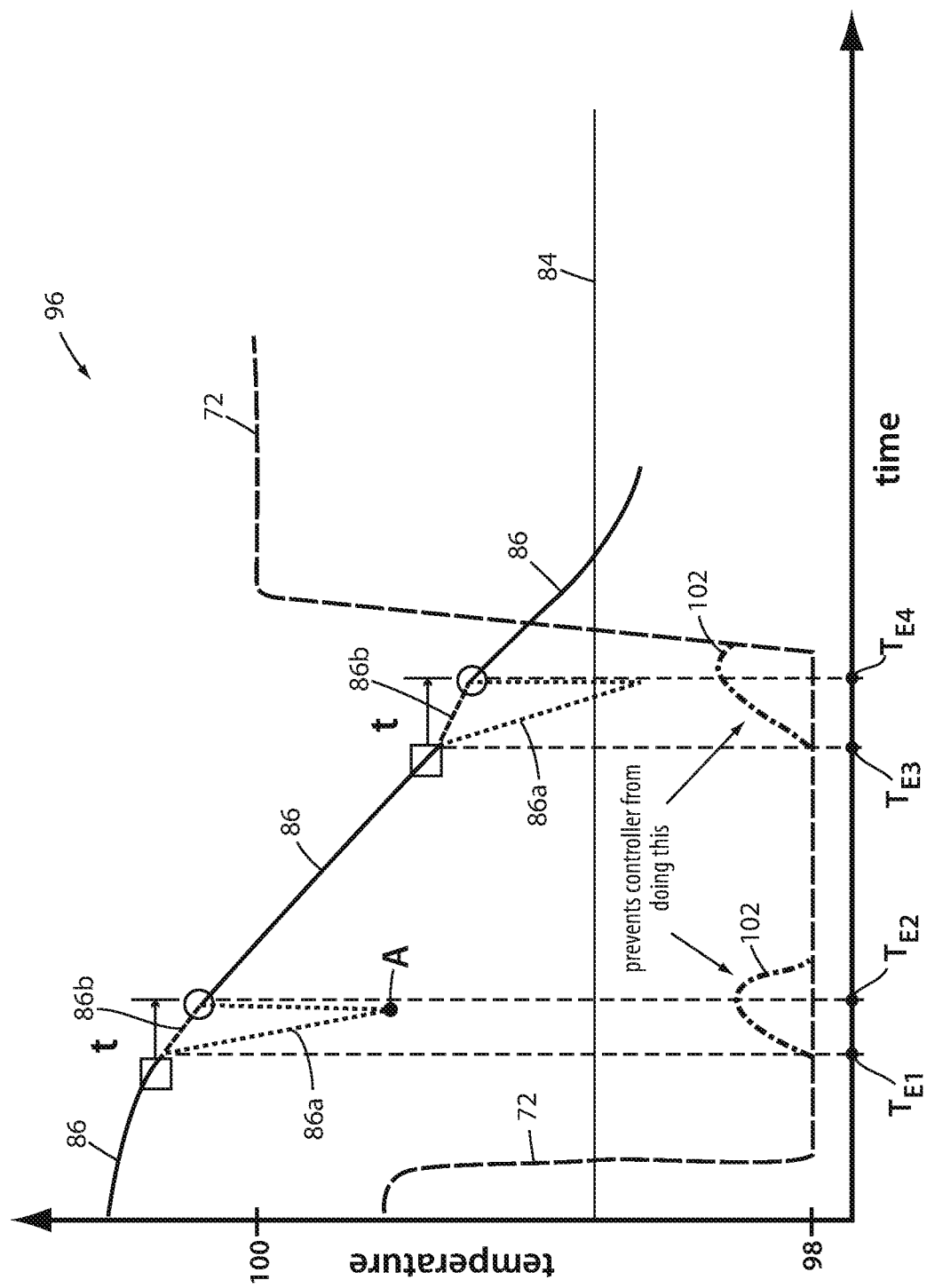
FIG. 5 is a graph of a patient target temperature, patient measured temperature, and fluid temperature illustrating a first manner of response of the thermal control unit to the administration of a fluid or medication to a patient.

An example of the possible effects of thermal contact between patient temperature probe 88 and medication or fluid administered to the patient can be seen more clearly in FIG. 5. FIG. 5 shows a graph 96 illustrating fluid temperature 72, patient temperature 86, and a patient target temperature 84 over time. As shown therein, the patient target temperature 84 is a constant value (typically set by a user using user interface 64). When the thermal therapy treatment shown in FIG. 5 begins, the fluid temperature is initially warmer than the patient target temperature 84, but cooler than the patient's measured temperature 86. Once the thermal treatment begins, controller 46 begins cooling the fluid temperature using control loops 70b and 70a. The cooling of the circulating fluid continues until, in the illustrated embodiment, the fluid reaches a predetermined minimum temperature 98 below which thermal control unit 22 does not lower the temperature of the circulating fluid. Minimum temperature 98 is designed as a safety temperature and may vary. In some embodiments, it may be set to about four degrees Celsius, although other temperatures may be selected. In some embodiments, controller 46 may also implement a predetermined maximum temperature 100 above which it does not heat the circulating fluid. The predetermined maximum is also implemented as a safety measure and may be set to about forty degrees Celsius, although other values may be selected.

As seen in FIG. 5, the result of the circulating fluid being cooler than the patient's temperature, as well as the cooling of the fluid's temperature by controller 46, the patient's temperature 86 begins to drop toward target temperature 84. At an arbitrary time $T_{E1}$ shown therein, a first event takes place. The precise nature of the first event may vary, but it includes the administration of medication and/or fluid to the patient at a location common to the location of patient temperature probe 88. Specifically, in the example shown in FIG. 5, the first event includes the administration of fluid or medication that has a temperature cooler than the patient's temperature. This causes the cooler fluid/medication to come into contact with the probe 88 and, as a result, the patient temperature readings 86 begin to show a sharp drop starting at time $T_{E1}$. These dropped temperature readings continue until time $T_{E2}$. $T_{E2}$ is the time at which the thermal effects of the administered medication and/or fluid have worn off. That is, $T_{E2}$ reflects the time when patient temperature probe 88 is once again reporting accurate indications of the patient's temperature (as opposed to temperature readings influenced by the temperature of the administered fluid or medication).

If pause/event control 66b is not activated by a user at or near the time of event $T_{E1}$, FIG. 5 illustrates via a dashed line 102 what would otherwise occur with respect to the fluid temperature 72. Specifically, dashed line 102 shows that controller 46 would warm the circulating fluid in response to the relatively sharp drop in the temperature readings from patient temperature probe 88 caused by the administration of the cooler medication and/or fluid. This is because the sharp drop in reported temperature readings 86 would causes controller 46 to start warming the circulating fluid in anticipation of the patient's temperature reaching target 84. This warming of the fluid temperature would continue until temperature readings reported by patient temperature probe 88 bottomed out at point A. After bottoming out at point A, the increase in the reported patient temperature readings would cause controller 46 to once again start cooling the circulating fluid. However, due to the thermal inertia of the system, the circulating fluid's temperature would likely not immediately decrease, but would instead likely start to decrease only after some time had passed subsequent to the patient's temperature bottoming out.

The result of the delivery of medication and/or fluid to the patient at a temperature different from the patient's temperature therefore causes controller 46, in the absence of the activation of pause/event control 66b, to make adjustments to the fluid temperature that are based on inaccurate readings of the patient's actual temperature. This not only causes thermal control unit 22 to waste energy, but it can slow down the speed at which thermal control unit 22 brings a patient to the target patient temperature 84. In the example of FIG. 5, this delay is caused by the fact that controller 46 has warmed the temperature of the fluid in response to what was perceived as a sharp drop in the patient's actual temperature, but was in fact a sharp drop in temperature due to the coldness of the administered fluid or medication and its cooling effect on patient temperature probe 88. Had the medication and/or fluid not been administered, controller 46 would not have warmed the fluid and the patient would have been cooled toward target temperature 84 more quickly.

The activation of pause/event control 66b allows controller 46 to substantially eliminate the delay caused by inaccurate patient temperature probe readings. When a user activates pause/event control 66b, controller 46 pauses using actual readings from patient temperature probe 88 in control loop 70b and instead uses assumed readings. The assumed readings, in some embodiments, are generated by predicting the patient's temperature. In other embodiments, the assumed readings are inferred from other factors and/or sensor readings that do not measure the patient's core temperature directly (e.g. the amount of heat transferred to/from the patient may be used to infer a patient temperature, either alone or in combination with a weight, a BMI reading, or another measurement of the patient's size). Further, in at least one embodiment where predicted patient temperature readings are used, the predicted patient temperature readings are based on a trend in the past patient temperature readings in the moments prior to the activation of pause/event control 66b. This is more easily understood with respect to FIG. 6.

Figure 6:
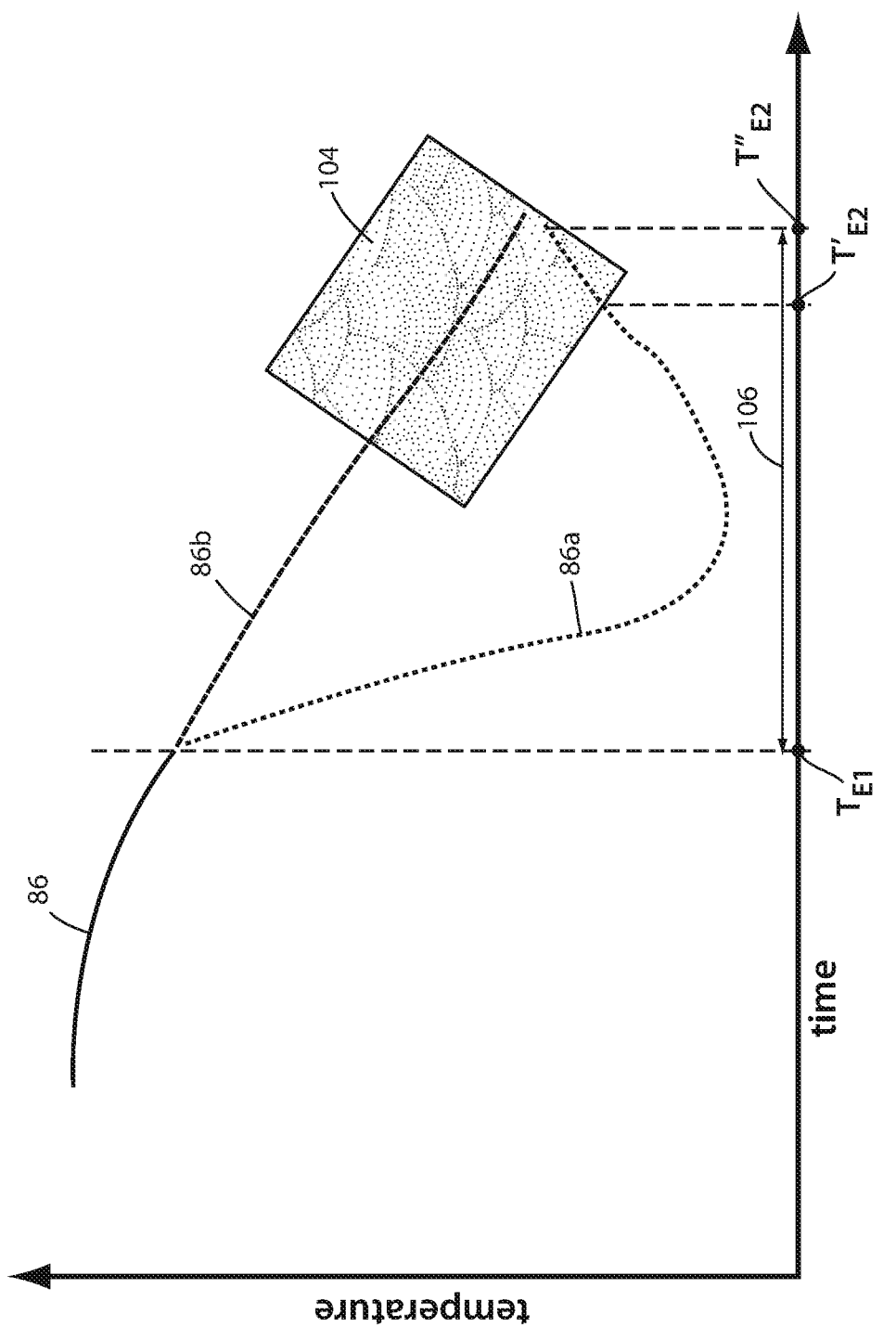
FIG. 6 is an enlargement of a portion of the graph of FIG. 5 illustrating inaccurate patient temperature readings and predicted patient temperature readings.

FIG. 6 shows an enlargement of the patient temperature readings 86 of FIG. 5 around the times between $T_{E1}$ and $T_{E2}$. As seen therein, FIG. 6 shows the actual patient temperature readings 86 prior to $T_{E1}$ as generally decreasing. At the time of $T_{E1}$, the reported patient temperature readings from patient temperature probe 88 begin to drop due to the administration of cold fluid or medication. As noted, these patient temperature readings are inaccurate because of the cold fluid or medication. These inaccurate patient temperature readings are indicated in FIG. 6 by the dashed line 86a. At the moment of $T_{E1}$, controller 46 calculates a set of predicted patient temperature values that are indicated in FIG. 6 by dashed line 86b. The predicted patient temperature readings 86b may be predicted in a variety of different ways. In one example, the slope of the actual patient temperature readings 86 in the moments prior to $T_{E1}$ is determined and a line with the same slope is extended forward from the patient temperature reading at time $T_{E1}$. In other words, the predicted temperature readings may simply be a linear extension of the rate at which the patient's temperature was dropping in the moments near $T_{E1}$. Other more sophisticated prediction techniques may be used, including, but not limited to, ones that examine not only the slope of the patient temperature readings 86 in the moments before $T_{E1}$, but also one or more derivatives of the slope, and/or other factors.

Regardless of the specific method used to predict the patient's temperature values 86b, controller 46 uses the predicted temperature values 86b with control loop 70b in response to the user activating pause/event control 66b. The use of predicted temperature values 86b with control loop 70b continues for a predefined amount of time. This predefined amount of time is intended by controller 46 to be equal to time $T_{E2}$, which, as noted, is the amount of time it takes until the thermal effects of the contact between the temperature probe 88 and the medication and/or fluid have worn off. Controller 46 determines this predefined amount of time in either of two manners. In a first manner ($T'_{E2}$), the predefined amount of time lasts until the inaccurate readings 86a from patient temperature probe 88 return to within a threshold range 104 of the predicted patient temperature values 86b. In a second manner ($T''_{E2}$), the predefined amount of time lasts until a fixed amount of time 106 passes from $T_{E1}$. Either of these manners, as well as still others, may be used for determining when the predefined time period ends.

Regardless of which specific method is used to determine the end of the predefined time period $T_{E2}$, controller 46 switches back to using the patient temperature readings 86 from patient temperature probe 88 in control loop 70b when the predefined time period ends. In other words, at time $T_{E2}$, controller 46 concludes that the readings from patient temperature probe 88 are no longer inaccurate (readings 86a), and therefore starts to use them again as inputs into control loop 70b. Thus, in the example shown in FIG. 6, controller 46 uses readings 86 in control loop 70b until time $T_{E1}$. After time $T_{E1}$, controller 46 uses predicted readings 86b in control loop 70b until the predefined time period expires. Depending on how the predefined time period is defined, controller 46 therefore uses predicted readings 86b from $T_{E1}$ to either $T'_{E2}$ or $T''_{E2}$. After that, controller 46 resumes using the readings 86 received from patient temperature probe 88.

The result of using the predicted temperature readings 86b during the predefined time period instead of the actual, but inaccurate, readings 86a is that controller 46 substantially ignores the changes in the temperatures reported from probe 88 that are caused by the different temperature of the administered fluid or medication. Although the predicted temperatures 86b that are used during this predefined time period may not accurately reflect the patient's actual temperature during this time period, they are a better reflection of the patient's actual temperature than the temperature readings reported by probe 88. Consequently, the actions carried out by controller 46 in controlling the temperature of the circulating fluid during this predefined time period are more responsive to the actual patient's temperature, and this more accurate response reduces delays that would otherwise likely occur in bringing the patient to the desired temperature, reduces energy that would otherwise likely be wasted, and/or helps thermal control unit 22 more smoothly maintain a patient's temperature at the desired temperature.

Although FIG. 6 illustrates an example of fluid or medication being administered to a patient that has a colder temperature than the patient's temperature, it will be understood that the same principles can be applied when fluid or medication is administered to the patient that is warmer than the patient's temperature. Further, it will also be understood that the pause/event control 66b is only desirably activated by a user when medication or fluid is administered to a patient at a location where the medication or fluid will affect the temperature readings reported by patient temperature probe 88. Thus, for example, if patient temperature probe 88 is a rectal probe and cold or warm medicine is administered to the patient via the esophagus, there is no need to activate pause/event control 66b in response to this medicine administration because the rectal probe will not come in contact with the administered medicine.

Although pause/event control 66b has been described herein as pausing the use of patient temperature readings 86a during a predefined time period, it will be understood by those skilled in the art that thermal control unit 22 may be modified to allow a user to change the predefined time period. For example, user interface 64 may be modified in some embodiments to allow a user to shorten or lengthen the predefined time period. This user-adjustability may be useful in situations where the user does not immediately activate control 66b after administering the fluid or medication. If the user happens to be delayed for a few minutes after administering fluid or medication to the patient before he or she activates control 66b, the user may wish to shorten the predefined time period to accommodate for the delay in activating control 66b. In some instances, the user is able to specify the new length of the predefined time period, while in other instances, the user is able to input the actual time at which medicine or fluid was administered. In the latter case, controller 46 may be configured to use the actual time entered when generating the predicted patient temperature readings 86b. That is, controller 46 may be configured to use only those readings from probe 88 that occurred before the entered time when predicting temperatures 86b in recognition that the readings from probe 88 that occurred after the entered time are likely inaccurate measurements of the patient's temperature.

FIG. 5 also illustrates the fact that pause/event control 66b can be activated multiple times during the course of a patient's thermal therapy. Specifically, FIG. 5 shows a second event occurring at time $T_{E3}$. The second event refers to the administering of medication and/or fluid to the patient for a second time. If the user does not activate pause/event control 66b at time or near time $T_{E3}$, controller 46 will likely control heat exchanger 38 in a manner that causes the fluid temperature to rise in the manner shown by the second dotted line 102. However, if the user does activate pause/event control 66b at or near time $T_{E3}$, controller 46 will generate a set of predicted patient temperatures 86b and use those predicted patient temperatures in control loop 70b until time $T_{E4}$ is reached. Time $T_{E4}$ may be defined in any of the same manners as time $T_{E2}$. That is, it may be a fixed amount of time 106 after time $T_{E3}$, it may be a variable amount of time that lasts until the readings from patient temperature probe 88 return to within a threshold range 104 of the predicted readings 86b, or it may be defined in a different manner.

In some embodiments, controller 46 is configured to issue an alarm if the patient's temperature changes by more than a predefined criterion, such as at a rate greater than a predefined limit. The purpose of the alarm is to ensure patient safety and to prompt users of thermal control unit 22 to investigate whether the reported steep change in the patient's temperature is actual, or caused by something other than the patient's actual temperature. In some instances, the rate of temperature change that prompts this alarm is set such that the alarm may be triggered when medication or fluid is administered to the patient at a location adjacent patient temperature probe 88. This is because the different temperature of the fluid or medication causes the temperature readings reported by the probe 88 to shift suddenly.

In order to avoid this alarm, controller 46 is configured in some embodiments to automatically suppress this patient temperature alarm whenever pause/event control 66b is activated. The suppression of this patient temperature alarm continues, in some embodiments, for the same amount of time that controller 46 uses assumed patient temperature readings 86b. That is, in some embodiments, it continues for the time from $T_{E1}$ to $T_{E2}$. In other embodiments, the time period of the suppressed patient temperature alarm is different.

Still further, in some embodiments, rather than suppressing completely the alarm indicating an excessive rate of change in the patient's temperature, controller 46 is configured to use a different threshold for alarming during the time period between $T_{E1}$ and $T_{E2}$. For example, if controller 46 is configured to issue an alarm if the patient's temperature changes by more than X degrees per minute when control 66b is not activated, controller 46 may be configured to only issue the alarm after control 66b is activated if the patient's temperature (as reported by probe 88) changes by more than Y degrees per minute, where Y is a higher number than X. The switching of the alarm threshold is temporary and, as noted, may continue for the same amount of time as the predefined time period discussed above, or it may continue for a different amount of time.

In other embodiments, a control separate from control 66 may be included on user interface 64 that temporarily suppresses and/or changes the criteria for the patient temperature alarm. In such embodiments, the user is able to utilize the alarm suppression option (or threshold change option) independently from the pause/event control 66b. In other words, pause/event control 66b can be activated by itself, the alarm suppression can be activated by itself, or they can both be activated together. In any embodiment, the alarm suppression may be complete, or it may be partial (e.g. a reduced volume, issued only locally and not remotely, etc.)

FIG. 7 shows another graph 108 illustrating another feature of thermal control unit 22. The graph includes an example of a patient's temperature 86, the fluid temperature 72 of the circulating fluid inside thermal control unit 22, and the target temperature 84 of a patient undergoing thermal treatment when thermal control unit 22 is operating in the automatic mode. Graph 108 differs from graph 96 of FIG. 5 in that FIG. 5 illustrates how thermal control system 20 responds when pause/event control 66b is activated while FIG. 7 illustrates how thermal control system 20 responds when medication control 66c is activated. Medication control 66c is activated after a patient is treated with certain types of medication, as will be explained in more detail below.

Medication control 66c is activated in order to allow thermal control unit 22 to better account for the pharmacological effects of patient medication on the thermal treatment of the patient. This differs from pause/event control 66b, which is activated in order to better account for the physical effects of the medication's temperature (or the fluid's temperature) on patient temperature probe 88. In other words, control 66b addresses how medication at a different temperature than patient temperature probe 88 affects the readings from patient temperature probe 88 when the medication comes into physical contact with patient temperature probe 88, while control 66c addresses how the medication (regardless of its temperature and the physical location at which it is administered) affects the patient's thermal physiology.

It is known that certain types of medication administered to a patient change the patient's responsiveness to thermal therapy. For example, if a patient is being cooled by thermal control unit 22 and is given a sedative, the sedative will typically allow thermal control unit 22 to reduce the patient's temperature more quickly than it otherwise would do so in the absence the sedative. Similarly, if a patient is given a paralytic medication to help prevent or stop patient shivering, the paralytic will typically cause the patient's temperature to drop more quickly than it would in the absence of the paralytic.

Medication control 66c is activated by a user when medicine is given to the patient that will have an effect on the patient's temperature, such as, but not limited to, a sedative or paralytic. When activated, controller 46 is adapted to adjust its control of the temperature of the circulating fluid in a manner that is more responsive to the likely effects of the medication and that helps prevent overshoot of the patient's temperature. Overshoot refers to the excessive warming or cooling of a patient after the patient's target temperature 84 is reached. Thus, for example, if a patient is cooled one degree below the target temperature 84, the cooling overshoot is one degree. To rectify this, thermal control unit 22 thereafter attempts to warm the patient back up the one degree to target temperature 84. However, if the patient warms up past target temperature 84, there is a warming overshoot.

Controller 46 is programmed to respond to the activation of medication control 66c, in some embodiments, in different manners, depending upon the different medication or different types of medications administered to the patient. In such embodiments, user interface 64 may be configured to request that a caregiver enter the name of the medication administered to the patient and/or the type of medication administered. In some such embodiments, user interface 64 may be programmed to also request an amount of the medication administered, and/or other information that affects the likely thermal response of the patient to the medication, such as, but not limited to, the weight of the patient, the body mass index of the patient, and/or other factors. In some embodiments, the thermal control unit 22 includes a bar code scanner, or the like, that automatically reads a bar code or other information from the label of a medication in order to determine the type of medication, amount of medication, and/or other information about the medication. In such latter embodiments, the thermal control unit 22 may be modified such that the reading of information from a medication label via the bar code scanner, or the like, automatically activated medication control 66c, thereby relieving the caregiver of the task of manually activating this control.

Controller 46 is programmed to use the information input by a caregiver when control 66c is activated in order to adjust the cooling or heating of the circulating fluid in a manner that anticipates the likely effect of the administered medication on the patient. One example of this programming is shown in more detail in FIG. 7. At a time $T_{E5}$, a sedative is administered to a patient undergoing thermal treatment using thermal control unit 22. The sedative is predicted by controller 46 to drop the patient's temperature more precipitously than it would in the absence of the sedative.

In at least one embodiment, in order to better prevent and/or reduce any overshoot in the patient's temperature, controller 46 determines at time $T_{E5}$ the current difference between the patient's temperature and the target temperature and the rate of change of this difference. Controller 46 uses this difference and its rate of change to determine a likely rate and/or temperature path that the patient will follow in reaching the target temperature 84, in the absence of the sedative, were controller 46 to continue to control heat exchanger 38 using control loops 70a and 70b. This path 86c is illustrated in dashed lines in FIG. 7. Controller 46 thereafter repetitively compares the patient's actual temperature to the predicted temperature and determines if the patient's temperature is dropping at an accelerated rate due to the medication. If it is, controller 46 warms the circulating fluid sooner than it otherwise would. If it is not, controller 46 stops or reduces the warming, such as shown by temperature line 72a in FIG. 7.

In some embodiments, controller 46 calculates a predicted effect of the sedative on the patient's temperature and determines how much earlier the patient will likely reach the target temperature due to the pharmacological effect of the sedative. The predicted pharmacological effect is determined using one or more of the following: previous administrations of the sedative on prior patients who were treated using thermal control unit 22 and whose data is stored in an accessible memory by controller 46, previously gathered data of the effects of the sedative from other thermal control units and/or from published literature, or other techniques. Thereafter, controller 46 adjusts the commands sent to heat exchanger 38 in order to anticipate the earlier arrival of the patient at the target temperature. As shown in FIG. 7, the earlier expected arrival of the patient at the target temperature causes controller 46 to begin warming the circulating fluid sooner than it otherwise would. Specifically, at or shortly after $T_{E5}$, controller 46 begins warming the circulating fluid, as shown by the upward rise in fluid temperature 72. At an evaluation point $T_{E6}$, controller 46 evaluates the drop in the patient's temperature. If the drop is consistent with the predicted drop caused by the sedative, controller 46 continues to warm the circulating fluid, as shown by solid line 72. However, if the patient's temperature has dropped less than predicted, controller 46 returns to cooling the patient in a manner indicated by dashed line 72a.

Dashed line 72a may reflect fluid temperatures resulting from controller 46 cooling the circulating fluid as if no sedative had been administered, or it may reflect fluid temperatures resulting from controller 46 cooling the circulating fluid as if the sedative had been administered but with reduced effect. In other words, dashed line 72a may represent controller 46 cooling the circulating fluid using a revised predicted effect of the sedative on the patient's temperature wherein the revised predicted effect is less than the original predicted effect. At a subsequent time, controller 46 may then compare the patient's actual temperature to that predicted using the revised predicted effect, and if the revised predicted effect and actual temperature vary by more than a threshold, make further revisions to revised predicted effect In another embodiment, controller 46 is programmed to adjust the derivative coefficient $K_D$ and/or the error values ($T_P$) used in the derivative step 92 of control loop 70b in response to the administration of a medication, such as a sedative. The adjustments use values that anticipate a greater negative slope in the patient's temperature (i.e. a more precipitous drop in the patient's temperature than would otherwise occur). The result is that controller 46 anticipates the pharmacological effect of the medication on the patient's temperature and makes adjustments to the temperature of the circulating fluid sooner than would otherwise occur. This helps to reduce overshoot in the patient's temperature.

The overall result of the reaction of controller 46 to the administration of a sedative, or other medication, to the patient is such that, when the patient's temperature reaches the target patient temperature at time $T_{E7}$, the temperature of the fluid 72 is also close to the target temperature, and there is no delay in waiting for heat exchanger 38 to heat up the circulating fluid to a value close to the patient target temperature. By having the circulating fluid temperature 72 near the patient target temperature 84 at or near the moment the patient reaches this target temperature, the probability of overshoot and/or the extent of any overshoot is greatly reduced. Further, because controller 46 has accounted for the increased cooling effect of the medication on the patient's temperature, there is also no delay in reducing the patient's temperature to the target temperature 84. The result therefore achieves reduced overshoot without any slowdown in the rate at which the patient's temperature is brought to the target temperature 84.

It will be understood by those skilled in the art that controller 46, when predicting the effect of a medication on a patient, may use not only the trend of previously measured patient temperatures prior to the administration of the medication, but also multiple additional pieces of information. These multiple additional pieces of information include data from prior clinical studies of specific medications and/or types of medications, published data for particular medications, patient data (e.g. height, weight, BMI, etc.) previously stored patient temperature data gathered by thermal control unit 22 from previous thermal treatments and stored in a memory of thermal control unit 22, and/or other sources.

Thermal control unit 22 may also be configured to implement an automatic temperature adjustment feature that automatically adjusts the patient target temperature based upon an administered medication. Some medications are desirably administered to a patient when the patient, or a portion of the patient's body where the medication is administered, is at a specific temperature. In order to implement this feature, user interface 64 may be modified to include another control 66d that, when activated, informs controller 46 that a medication has been administered to the patient that has a target temperature associated with it. Control 66d includes, in some embodiments, the ability for a user to identify the specific medication administered to the patient. In response to the activation of control 66d, controller 46 accesses a memory on board thermal control unit 22 that stores desired temperatures for particular medications. Controller 46 uses this memory to look up the desired patient temperature corresponding to the particular medication identified by the user as having been administered to the patient. Controller 46 then resets the patient target temperature 84 to the desired temperature corresponding to the administered medication. The new patient target temperature 84 is thereafter used by control loop 70b so that the patient's temperature is adjusted by thermal control unit 22 toward the new patient target temperature.

In some embodiments, controller 46 is programmed to respond to control 66d by changing the patient target temperature for only a predetermined amount of time. The predetermined time may correspond to the amount of time the patient's temperature is held at the new target temperature in order for the medication to be most effective. In other words, if medication A is desirably administered to a patient whose temperature stays at 35 degrees Celsius for four hours, then controller 46 automatically switches the target patient temperature back to its previous value after the passage of four hours. The particular times at which a patient's temperature is held at a new desired target temperature may be stored in the same memory that stores the target temperatures themselves. These values may be taken from published literature and/or from recommendations from the manufacturer of the individual medications. Alternatively, the automatic temperature adjustment feature of control 66d may be configured to allow a user to specify the length of the predetermined amount of time.

In some embodiments, thermal control unit 22 is adapted to deliver fluid at different temperatures to different thermal pads 24. For example, thermal control unit 22 is adapted, in some embodiments, to be able to deliver fluid at temperature X to a first outlet port 44 and fluid at temperature Y to a second (or third) fluid outlet port 44. The different fluid outlet ports 44 are in fluid communication with thermal pads 24 that are positioned at different locations on the patient's body. In some situations, one or two thermal pads 24 are positioned on the patient's legs while another is wrapped around the patient's torso. In such embodiments, thermal control unit 22 is adapted to adjust the patient target temperatures 84 for the different portions of the patient's body independently. That is, the temperature controlled fluid delivered to the patient's legs may have a different temperature than the temperature controlled fluid delivered to the patient's torso. Alternatively, it may be desirable in some situations to deliver fluid of different temperature to the patient's legs. In still other embodiments, the thermal pads 24 may be positioned at other locations on the patient's body, and fluid of different temperature may be delivered to the different body parts.

In at least one embodiment of thermal control unit 22 that is configured to deliver fluid at multiple temperatures, controller 46 is adapted to automatically alter the patient target temperature for a particular portion of the patient's body in response to the activation of control 66d. Thus, for example, if a patient is undergoing thermal treatment with thermal control unit 22 and a medication is applied to a local portion of the patient's body, e.g. to the patient's right leg, controller 46 is programmed—in response to activation of control 66d—to alter the patient target temperature for the patient's right leg while leaving the patient's target temperature for the rest of the patient's body unadjusted. In this manner, thermal control unit 22 automatically adapts to the administration of particular medications to a local area of the patient's body by adjusting the patient's temperature in that particular local area to a target temperature that is desirable for the administered medication. Control 66d can therefore be used to either automatically adjust the target temperature of the patient's entire body, or only a portion of the patient's body, in response to the administration of medication.

It will be understood that although thermal control unit 22 has been described herein as having all four controls 66a, 66b, 66c, and 66d, thermal control unit 22 can be modified to include fewer of these controls. Indeed, thermal control unit 22 can be modified to include control 66a in combination with any one or more of controls 66b, 66c, and/or 66d. In some embodiments, the controls 66a-d are incorporated into thermal control unit 22 in such a way that each control operates separately and independently from the other control. However, in some embodiments, the functions of more than one of the controls may be combined together. For example, in one modified embodiment, if a user activates both pause/event control 66b and medication control 66c, controller 46 is programmed to use predicted values of the patient's temperature 86b in control loop 70b wherein the predicted values take into account the pharmacological effect of the medication administered to the patient (based on experimental data previously gathered and stored in an accessible memory). As a result, controller 46 will use a different set of predicted patient temperature values than it would otherwise use if only control 66b were activated (and not control 66c). Still other types of overlap in functions may be implemented when more than one control 66 is activated.

It will be understood that thermal control unit 22 can be modified from what has been shown and described herein in a variety of other manners. For example, thermal control unit 22 may also be modified to include one or more flow sensors that measure the rate of fluid flow and report this information to controller 46. In such modified embodiments, controller 46 uses the flow rate in determining what heating/cooling commands to send to heat exchanger 38 and/or what flow rate signals to send to pump 32.

The particular order of the components along circulation channel 34 of control unit 22 may also or alternatively be varied from what is shown in FIG. 3. For example, although FIG. 3 depicts pump 32 as being upstream of heat exchanger 38 and air separator 58 as being upstream of pump 32, this order may be changed. Air separator 58, pump 32, heat exchanger 38 and reservoir 62 may be positioned at any suitable location along circulation channel 34. Indeed, in some embodiments, reservoir 62 is moved so as to be in line with and part of circulation channel 34, rather than external to circulation channel 34 as shown in FIG. 3, thereby forcing the circulating fluid to flow through reservoir 62 rather than around reservoir 62.

Further details regarding the construction and operation of one embodiment of thermal control unit 22 that are not described herein are found in commonly assigned U.S. patent application Ser. No. 14/282,383 filed May 20, 2014, by inventors Christopher Hopper et al. and entitled THERMAL CONTROL SYSTEM, the complete disclosure of which is incorporated herein by reference.

User interface 64 of thermal control unit 22 can take on a wide variety of different forms. For example, although pause/event control 66b has been described herein primarily as a dual-function control in which the use of temperature probe readings is paused and event information is entered, it will be understood that these functions can be separated. For example, in at least one embodiment, pause/event control 66b is replaced with an event control 66b that, when activated, allows a caregiver to enter event information (such as the use of cleaning fluid at the site of the temperature probe 88 or the administration of medication at that site, etc.). Further, when this event information is entered, controller 46 automatically activates the pause function. As yet another alternative, controls two or more of controls 66b, 66c, and 66d can be combined into a single control that, when activated, prompts the user to input further information about the event taking place. Controller 46 then either automatically activates the appropriate function associated with one of controls 66b-d based on the entered event data, or presents on a touch screen display an option for the caregiver to activate the desired control. Still other variations may be implemented for activating one or more of the controls 66b-d.

User interface 64 may also be modified to allow a user to enter event data indicating that patient temperature probe 88 is being temporarily removed or readjusted. For example, probe 88 may be removed for cleaning purposes, or it may be removed in order to provide clearance for a medical procedure and/or to administer medication, and/or for other purposes. In such situations, the readings from probe 88 while it is positioned outside the patient's body, or while it is being cleaned, or while it is otherwise being adjusted, will likely not be accurate. User interface 64 may therefore be modified to include an additional control (e.g. 66e, not shown) for such situations, or control 66b can be modified such that, when activated, a user can identify this particular event to controller 46. In such events, controller 46 is programmed to act in the same manner as when control 66b is activated, except instead of acting in this manner for a predefined amount of time, controller 46 acts in this manner until the user indicates via user interface 64 that the probe 88 has been returned to the patient, the cleaning of probe 88 is done, or whatever the event was that led to the inaccurate temperature readings from probe 88 is otherwise completed. Thermal control unit 22 can therefore be modified to both start and stop using assumed temperature readings based on manual inputs from the user (in addition to automatically starting and/or stopping the use of assumed temperatures). Still other modifications are possible.

Various additional alterations and changes beyond those already mentioned herein can be made to the above-described embodiments. This disclosure is presented for illustrative purposes and should not be interpreted as an exhaustive description of all embodiments or to limit the scope of the claims to the specific elements illustrated or described in connection with these embodiments. For example, and without limitation, any individual element(s) of the described embodiments may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Any reference to claim elements in the singular, for example, using the articles "a," "an," "the" or "said," is not to be construed as limiting the element to the singular.

What is claimed is:

1. A thermal control unit for controlling a temperature of a patient, the thermal control unit comprising:
   a fluid outlet adapted to fluidly couple to a fluid supply line;
   a fluid inlet adapted to fluidly couple to a fluid return line;

a circulation channel coupled to the fluid outlet and the fluid inlet;

a pump for circulating fluid through the circulation channel from the fluid inlet to the fluid outlet;

a heat exchanger for controlling a temperature of the circulating fluid in the circulation channel;

a fluid temperature sensor adapted to sense the temperature of the circulating fluid;

a patient temperature probe port adapted to receive patient temperature readings from a patient temperature probe;

a user interface including a pause control and a patient target temperature input; and a controller in communication with the patient temperature probe port, the fluid temperature sensor, and the user interface, the controller adapted to use the patient temperature readings to control the temperature of the circulating fluid when the pause control is not activated, and to pause using the patient temperature readings to control the temperature of the circulating fluid when the pause control is activated while the controller continues to pump the circulating fluid out of the fluid outlet to the patient.

2. The thermal control unit of claim 1 wherein the controller pauses for a predefined amount of time, and thereafter resumes utilizing the patient temperature readings to control the temperature of the circulating fluid.

3. The thermal control unit of claim 1 wherein the controller sets a target temperature of the circulating fluid to a value that is based on a current patient temperature reading when the pause control is not activated and the controller sets a target temperature of the circulating fluid to a value that is based on a previous patient temperature reading when the pause control is activated.

4. The thermal control unit of claim 1 wherein the controller is adapted to use the patient temperature readings to control the temperature of the circulating fluid when the pause control is not activated and to use assumed patient temperature readings when the pause control is activated.

5. The thermal control unit of claim 1 wherein the controller records a patient temperature reading when pausing the use of patient temperature readings to control the temperature of the circulating fluid, and the controller pauses until a current patient temperature reading returns to within a threshold of the recorded patient temperature reading.

6. The thermal control unit of claim 1 wherein the user interface is adapted to allow a user to input event data regarding a patient treatment event and the pause control is automatically activated when event data is input into the user interface, and wherein the event data includes at least one of the following: a particular medication administered to the patient and fluid administered to the patient at a location adjacent to the patient temperature probe.

7. The thermal control unit of claim 6 wherein the controller pauses using the patient temperature readings for varying amounts of time based on at least one of the particular medication and an amount of the particular medication.

8. A thermal control unit for controlling a temperature of a patient, the thermal control unit comprising:

a fluid outlet adapted to fluidly couple to a fluid supply line;

a fluid inlet adapted to fluidly couple to a fluid return line;

a circulation channel coupled to the fluid outlet and the fluid inlet;

a pump for circulating fluid through the circulation channel from the fluid inlet to the fluid outlet;

a heat exchanger for controlling a temperature of the circulating fluid in the circulation channel;

a fluid temperature sensor adapted to sense the temperature of the circulating fluid;

a patient temperature probe port adapted to receive patient temperature readings from a patient temperature probe;

a user interface adapted to receive a patient target temperature and event data regarding a patient treatment event; and a controller in communication with the patient temperature probe port, the fluid temperature sensor, and the user interface, the controller adapted to issue an alarm if the patient temperature readings deviate from a predefined criterion when no event data is entered via the user interface, and the controller adapted to not issue the alarm if the patient temperature readings deviate from the predefined criterion when event data is entered via the user interface.

9. The thermal control unit of claim 8 wherein, when event data is entered via the user interface, the controller does not issue the alarm for a predefined time period.

10. The thermal control unit of claim 9 wherein the predefined time period lasts until a current patient temperature reading returns to within a threshold of a previous patient temperature reading recorded prior to the event data being entered.

11. The thermal control unit of claim 9 wherein, after expiration of the predefined time period, the controller issues the alarm if the patient temperature readings deviate from the predefined criterion.

12. The thermal control unit of claim 9 wherein the controller uses the patient temperature readings to control the temperature of the circulating fluid when no event data is received, and to pause using the patient temperature readings to control the temperature of the circulating fluid when event data is received.

13. The thermal control unit of claim 12 wherein the controller is adapted to continue to pump the circulating fluid out of the fluid outlet to the patient while the controller pauses its use of the patient temperature readings to control the temperature of the circulating fluid when event data is received; and the controller is further adapted to pause its use of the patient temperature readings to control the temperature of the circulating fluid for the predefined time period.

14. The thermal control unit of claim 12 wherein the controller sets a target temperature of the circulating fluid to a value that is based on a current patient temperature reading when no event data is received and the controller sets the target temperature of the circulating fluid to a value that is based on a previous patient temperature reading when event data is received.

15. The thermal control unit of claim 14 wherein the controller records a patient temperature reading when pausing the use of the patient temperature readings to control the temperature of the circulating fluid, and the controller pauses until the current patient temperature reading returns to within a threshold of the recorded patient temperature reading.

16. A thermal control unit for controlling a temperature of a patient, the thermal control unit comprising:

a fluid outlet adapted to fluidly couple to a fluid supply line;

a fluid inlet adapted to fluidly couple to a fluid return line;

a circulation channel coupled to the fluid outlet and the fluid inlet;

a pump for circulating fluid through the circulation channel from the fluid inlet to the fluid outlet;

a heat exchanger for controlling a temperature of the circulating fluid in the circulation channel;

a fluid temperature sensor adapted to sense the temperature of the circulting fluid;

a patient temperature probe port adapted to receive patient temperature readings from a patient temperature probe;

a user interface adapted to receive a patient target temperature and event data regarding a patient treatment event; and a controller in communication with the patient temperature probe port, the fluid temperature sensor, and the user interface, the controller adapted to use the patient temperature reading to control the temperature of the circulating fluid when no event data is received, and to use assumed patient temperature readings when event data is received.

17. The thermal control unit of claim 16 wherein the assumed patient temperature readings are generated by the controller based upon a trend in the patient's temperature readings prior to the event data being received.

18. The thermal control unit of claim 17 wherein the controller uses the assumed patient temperature readings for a predefined time period to determine a target temperature for the circulating fluid, and the controller predicts a patient temperature reading at an expiration of the predefined time period.

19. The thermal control unit of claim 18 wherein the predefined time period is one of a fixed amount of time and a variable amount of time that lasts until a current patient temperature reading falls within a predefined range of the predicted patient temperature, and wherein the event data indicates at least one of administration of a medication to the patient and supplying fluid to the patient at a location adjacent the patient temperature probe.

* * * * *

UNITED STATES PATENT AND TRADEMARK OFFICE
CERTIFICATE OF CORRECTION

| | | |
|---|---|---|
| PATENT NO. | : 11,311,413 B2 | Page 1 of 1 |
| APPLICATION NO. | : 16/169271 | |
| DATED | : April 26, 2022 | |
| INVENTOR(S) | : Gregory S. Taylor et al. | |

It is certified that error appears in the above-identified patent and that said Letters Patent is hereby corrected as shown below:

In the Claims

Column 21
Claim 3, Line 31: "a" should be --the-- before "target temperature"

Column 23
Claim 16, Line 6: word "circulting" should be --circulating--

Column 23
Claim 16, Line 15: "reading" should be --readings--

Signed and Sealed this
Thirtieth Day of April, 2024

*Katherine Kelly Vidal*

Katherine Kelly Vidal
*Director of the United States Patent and Trademark Office*